United States Patent [19]

Strutz

[11] Patent Number: 5,510,512

[45] Date of Patent: Apr. 23, 1996

[54] PROCESS FOR PREPARATION OF 2-(DIALKOXYMETHYL)-CARBOXYLIC ACID ESTERS

[75] Inventor: Heinz Strutz, Frankfurt am Main, Germany

[73] Assignee: Hoechst Aktiengesellschaft, Frankfurt am Main, Germany

[21] Appl. No.: 339,639

[22] Filed: Nov. 14, 1994

Related U.S. Application Data

[63] Continuation of Ser. No. 84,183, filed as PCT/EP91/02388, Dec. 12, 1991, abandoned.

[30] Foreign Application Priority Data

Jan. 5, 1991 [DE] Germany .......................... 41 00 178.8

[51] Int. Cl.⁶ .................................................. C07C 69/708
[52] U.S. Cl. ........................ 560/186; 560/184; 560/187
[58] Field of Search .................................... 560/187, 184, 560/186

[56] References Cited

U.S. PATENT DOCUMENTS

| | | | |
|---|---|---|---|
| 2,535,012 | 12/1950 | Croxall et al. | 260/484 |
| 4,501,705 | 2/1985 | Matsui et al. | 260/465.6 |
| 4,534,910 | 8/1985 | Peeters et al. | 260/465.6 |
| 5,130,435 | 7/1992 | Hoelderich et al. | 546/256 |

FOREIGN PATENT DOCUMENTS

| | | |
|---|---|---|
| 055108 | 12/1981 | European Pat. Off. . |
| 0327985 | 8/1989 | European Pat. Off. . |
| 3211679A1 | 6/1983 | Germany . |
| 3641605 | 6/1988 | Germany . |
| 60156643 | 1/1984 | Japan . |

OTHER PUBLICATIONS

Oxidations of Olefins with Alcoholic Palladium(II) Salts, W. G. Lloyd et al, Jan. 31, 1969, *Journal Organic Chemistry*, vol. 34, No. 12, p. 3949.

*Primary Examiner*—José G. Dees
*Assistant Examiner*—Barbara S. Frazier
*Attorney, Agent, or Firm*—Connolly & Hutz

[57] ABSTRACT

Process for the preparation of 2-(dialkoxymethyl)carboxylic acid esters of the formula I

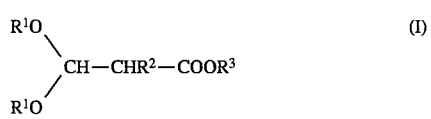

by oxidizing β-acetalization of acrylic acid esters with alcohols $R^1OH$, wherein $R^1$ has the meaning mentioned, in the presence of oxygen as the oxidant and of a catalyst system based on one or more metals of the platinum group and/or compounds thereof and of a copper compound, comprises carrying out the reaction at a temperature of up to 80° C. and in which the catalyst system contains 1 to 4 equivalents of anions, based on the sum of the metal atoms and metal cations, of which at most 3 equivalents are halide ions, the halogen having a molecular weight of at least 35.

19 Claims, No Drawings

PROCESS FOR PREPARATION OF 2-(DIALKOXYMETHYL)-CARBOXYLIC ACID ESTERS

This application is a continuation of application Ser. No. 08/084,183 filed Jul. 1, 1993, now abandoned, which is a 371 of PCT/EP91/02388 filed Dec. 12, 1991.

The invention relates to a process for the preparation of 2-(dialkoxymethyl)carboxylic acid esters of the formula I Compounds of the formula I are readily handlable, stable derivatives of formylacetic esters. They are employed as intermediates for the preparation of corresponding vinyl ethers and in the preparation of odoriferous substances, pharmaceuticals and plant protection preparations.

It is known to prepare 2-(dialkoxymethyl)carboxylic acid esters by reaction of orthoformic acid esters with ketene in the presence of $BF_3$ as a catalyst. In the process described (U.S. Pat. No. 2,449,471), compounds of the formula I where $R^2=H$ and $R^1=R^3$ are obtained. In practice, the ability to employ this process is greatly restricted, as the unstable ketene is only capable of limited storage. Other disadvantages of this process are that it is carried out using a high excess of ketene and only a low yield of about 55% is obtained. Furthermore, only "symmetrical" products where $R^1=R^3$ are obtainable in this manner. According to U.S. Pat. No. 2,535,012, 2-(dialkoxymethyl)carboxylic acid esters are prepared by reaction of acetylene with dialkyl carbonates under sodium alcoholate catalysis. The disadvantages here are the high excess of dialkyl carbonate to be used and the only moderate yields. Moreover, there are considerable problems in the distillative separation of the co-formed β-alkoxyacrylic acid ester (Houben/Weyl, Vol. VII/I, p. 109).

Furthermore, the addition of alcohols to the sodium salt of formylacetic ester in the presence of acid in excess (DE-A 3,641,605) or to β-alkoxy- or β-carbalkoxyacrylic acid esters (DE Offenlegungsschrift 3,211,679), which for their part are prepared from the sodium salt of formylacetic ester or by addition of alcohols or carboxylic acids to propiolic ester, is known. The use of the sodium salt of formylacetic ester has the disadvantage that stoichiometric amounts of alkali metal alcoholate, which must be formed from alkali metal, are needed for its preparation. Because of this, and owing to the necessary neutralization of the excess of acid, undesired amounts of salt are formed. The use of vinyl ethers and esters as a starting material for 2-(dialkoxymethyl)carboxylic acid esters is disadvantageous because of their multi-step and complicated preparation. In general, vinyl ethers are conversely even prepared from corresponding acetals by alcohol elimination (EP-A 0,327,985). According to JP-A 60/156,643, 2-(dialkoxymethyl)carboxylic acid esters can be prepared by acid-catalysed alcoholysis of β-alkoxy-β-carbamido-propionic acid esters. However, these are only to be obtained in a complicated manner by electrochemical oxidation of β-amidopropionic acid esters, which in turn are only accessible by addition of amines to acrylic acid esters in the presence of the corresponding acid anhydride or chloride.

According to EP-A 55,108, 2-(dialkoxymethyl)carboxylic acid esters are prepared by oxidation of acrylic acid esters in the presence of catalysts using alkyl nitrites in the presence of alcohol. The yields of the desired product, however, are below 10%; moreover an enormous excess of alkyl nitrite is needed (about 50-fold). If oxidation is carried out with air in the presence of $PdCl_2$ and $CuCl_2$, the yields fall even further to below 3%. The oxidation of acrylic esters with oxygen under these conditions has been described in J. Org. Chem. (1969) 34, 3949 as unsuitable even for the preparation of 2-(dialkoxymethyl)carboxylic acid esters.

The object was therefore to make available an improved process for the preparation of 2-(dialkoxymethyl)carboxylic acid esters which does not have the disadvantages mentioned.

It has now been found that acrylic acid esters can be converted and in high yields into the 2-(dialkoxymethyl)carboxylic acid esters by means of oxygen in the presence of metals of the platinum group and/or compounds thereof and copper compounds and also of alcohols if the catalyst system contains 1 to 4 equivalents of anions, based on the sum of the metal atoms and metal cations, of which at most 3 equivalents are halide ions. The oxygen can be employed in pure form or in the form of mixtures with inert gases, of the mixtures air preferably being employed.

The invention relates to a process for the preparation of 2-(dialkoxymethyl)carboxylic acid esters of the formula I, wherein $R^1$ is a non-aromatic hydrocarbon radical or a heterocyclic non-aromatic radical, which apart from oxygen, nitrogen and/or sulfur atoms in the ring only contains carbon and hydrogen atoms, and each of which has 1 to 20 carbon atoms, it being possible for the radical $R^1$ to carry 1 to 5 substituents and the substituents being identical or different and being halogen, an aryl, carbalkoxy, dialkylamino, diarylamino or cyano group or an alkoxy group, the alkyl being substituted or unsubstituted $C_1$- to $C_{12}$-alkyl, or is an aryloxy group, the aryl being substituted or unsubstituted $C_6$- to $C_{14}$-aryl, a substituted or unsubstituted benzyl or phenethyl radical or an $R^4O$—$(R^5O)_x$—$R^5$ group, where $R^4$ is substituted or unsubstituted $C_1$- to $C_{12}$-alkyl or $C_6$- to $C_{14}$-aryl, $R^5$ is a branched or unbranched hydrocarbon radical having 1 to 4 carbon atoms or phenylene and x=1 to 6, $R^2$ is hydrogen or alkyl having 1 to 5 carbon atoms and $R^3$ is unsubstituted or substituted $C_6$- to $C_{14}$-aryl or a radical mentioned under $R^1$, by oxidizing β-acetalization of acrylic acid esters with alcohols $R^1OH$ wherein $R^1$ has the meaning mentioned, under the action of oxygen as the oxidant and of a catalyst system based on one or more metals of the platinum group and/or compounds thereof and of a copper compound, which comprises carrying out the reaction at a temperature of up to 80° C. and in which the catalyst system contains 1 to 4 equivalents of anions, based on the sum of the metal atoms and metal cations, of which at most 3 equivalents are halide ions, the halogen having a molecular weight of at least 35.

The term acrylic acid ester in this connection also includes acrylic acid esters which are substituted in the α-position. Unsubstituted acrylic acid esters, however, are preferred.

The radical $R^3$ has no substantial influence on the reaction and can therefore in general be chosen arbitrarily, as long as it is inert under the reaction conditions.

The alcoholic reaction component can be freely chosen within wide limits and can be substituted in one or more positions by those functional groups which are inert under the oxidizing reaction conditions or with respect to self-reaction with the β-carbon atom oxidized in the reaction to the formal oxidation state +1.

Examples of the alcohol which may be mentioned are methanol, ethanol, n- and i-propanol, the various butanols, cyclohexanol, optionally substituted benzyl alcohol, optionally substituted phenethyl alcohol, 2-chloroethanol, 3-chloropropanol, monomethyl, -ethyl, -propyl, -butyl or -phenyl ethers of glycols and other dihydric alcohols or of polymerization products of alcohols of this type, 2-dimethylaminoethanol, N-(2-hydroxyethyl)formamide, 3-hydroxypropionitrile, glycolic acid esters and 3,3-dimethoxypropan-1-ol; aliphatic alcohols unbranched in the 1-position, such as methanol, ethanol, n-propanol, n-butanol and 2-methylpropanol are particularly preferred. However, mixtures of alcohols can also be employed. Glycol is here understood as meaning in particular ethylene glycol, propane-1,2-diol and butane-1,2-diol. Other dihydric alcohols which may be mentioned are, for example, propane-1,3-diol and butane-1,4-diol.

The alcohol, if it is present as a liquid at reaction temperature, can also serve as the solvent. If another solvent is used, the alcohol is preferably employed in an at least 2-fold molar amount, particularly preferably in an at least 8-fold molar amount, relative to the acrylic acid ester. The amount of solvent added is expediently proportioned such that the reaction mixture is readily handled. Solvents which can in particular be employed are aprotic polar compounds which are miscible with the reaction components or dissolve these without reacting with them, and which at least start to dissolve the catalyst. A reaction with the catalyst or co-catalyst in the sense of a coordination does not need to be excluded. Examples of such solvents are diethers of the abovementioned glycols and other divalent alcohols or aliphatic or aromatic nitriles. Dimethoxyethane, acetonitrile and benzonitrile are particularly preferred.

The components of the catalyst system are expediently employed as such or immobilized on a suitable support, such as alumina, silica gel or carbon. In the last case, the process can be carried out continuously. From the platinum metal group, palladium and its compounds are preferred. Palladium halides $PdX_2$ or palladium/nitrile complexes $PdX_2(NCR)_2$ in which the halogen X has a molecular weight of at least 35 and R is a hydrocarbon radical having 1 to 8 carbon atoms, preferably phenyl, are particularly preferred. Further compounds which may be mentioned are, for example, $Pd(CH_3COO)_2$ and palladium bisacetylacetonate. The metal of the platinum group and/or its compounds can advantageously be employed in a molar ratio of $10^{-5}$ to 10, preferably $10^{-4}$ to 0.2, particularly preferably $10^{-3}$ to 0.1, relative to the acrylic acid ester, the atomic ratio of the copper to the metal of the platinum group preferably being at least 1:1.

Compounds of copper in the oxidation state +1, which advantageously contain little or no water, are employed as co-catalysts. Halides and pseudohalides of copper in the oxidation state +1 are preferred. CuCl, CuBr and CuI are particularly preferred. The copper compound is advantageously employed in a molar ratio of $10^{-5}$ to 10, preferably $10^{-3}$ to 5, particularly preferably 0.01 to 1, relative to the acrylic acid ester. A fraction of the copper compound which may be present in the reaction medium undissolved can be recovered after the reaction. The catalyst system can be employed repeatedly with an appropriate reaction procedure.

The oxygen serves as the oxidant for converting the β-carbon atom of the acrylic acid ester from the oxidation state −2 to the oxidation state +1. The addition of the oxidant can be carried out, for example, by passing it over or passing it through. The oxidation can be carried out at atmospheric pressure or elevated pressure within the bounds of the regulations applying to use of air- or oxygen-hydrocarbon mixtures.

The reaction temperature is in general above −10° C., preferably between +10° and +70° C., particularly preferably between +20° and +55° C. Exceeding a reaction temperature of about 70° C., depending on the other reaction conditions, can have an unfavorable effect on the yield of 2-(dialkoxymethyl)carboxylic acid ester.

The reaction times are dependent on the other reaction parameters such as temperature, pressure and catalyst concentration and are in general in the region from, for example, 5 to 50 hours, usually 10 to 30 hours.

Working up is carried out by customary methods. It is non-problematical, as the reaction can easily be directed in such a way that the product is virtually free of the corresponding 3-alkoxyacrylic acid esters. Neutralization of the reaction mixture is not necessary, so that in contrast to the prior art no salt is produced during the working up.

Another advantage of the process according to the invention is that 2-(dialkoxymethyl)carboxylic acid esters of the general formula I can be prepared in a single step from easily accessible starting compounds which can be handled industrially without problems with an optimum reaction procedure in high yields of more than 80%, relative to the acrylic acid ester employed. This result is in particular surprising since the preparation of 2-(dialkoxymethyl)carboxylic acid esters from acrylic acid derivatives by oxidation with air in the presence of $PdCl_2$ and $CuCl_2$, as mentioned at the beginning, has previously only led to extremely poor yields.

EXAMPLES 1. 0.21 g (1.2 mmol) of $PdCl_2$, 1.2 g (12 mmol) of CuCl, 3.42 g (108 mmol) of methanol and 1.53 g (12 mmol) of butyl acrylate in 10.5 g of dimethoxyethane was stirred for 20 hours at 50° C. under an $O_2$ atmosphere ($O_2$-filled air balloon) in a round-bottomed flask with a magnet core and reflux condenser. After addition of 1.2 g of m-phenoxytoluene as internal standard, 1.57 g (8.2 mmol) of butyl 3,3-dimethoxypropionate (69% of theory) were found by gas chromatography. After filtration through basic $Al_2O_3$ (activity I; hexane/methyl t-butyl ether (1:1) as eluent), the volatile constituents were removed at 45° C./0.1 bar, and 1.62 g (8.5 mmol) of butyl 3,3-dimethoxypropionate (71% of theory) were found in the residue by $^1$H-NMR spectroscopy, in very good agreement with the gas chromatographic analysis.

2. to 8. The effects of the CuCl concentration, the reaction temperature and the reaction time were investigated analogously to Example 1. The results are compiled in Table 1.

TABLE 1

| Ex. | Weight (CuCl)(g) | T(°C.) | t(h) | Yield (%*) |
| --- | --- | --- | --- | --- |
| 2 | 0.6 | 50 | 20 | 76 |
| 3 | 0.3 | 50 | 20 | 67 |
| 4 | 0.6 | 40 | 20 | 81 |
| 5 | 0.3 | 40 | 20 | 86 |
| 6 | 0.3 | 30 | 20 | 82 |
| 7 | 0.15 | 40 | 30 | 78 |
| 8 | 0.6 | 70 | 20 | 28 |

*determined by gas chromatography; m-phenoxytoluene (1.2 g) as internal standard 9. and 10. 0.07 g (0.4 mmol) of $PdCl_2$, 4 mmol of a Cu compound corresponding to Table 2, 1.14 g (36 mmol) of methanol and 0.51 g of butyl acrylate in 3.5 g of dimethoxyethane was stirred for 20 hours at 50° C. under an $O_2$ atmosphere ($O_2$-filled air balloon) in a round-bottomed flask with a magnetic core and reflux condenser. The yields of butyl 3,3-dimethoxypropionate as a function of the Cu compound used are compiled in Table 2.

TABLE 2

| Ex. | Cu compound | Yield (%*) |
| --- | --- | --- |
| 9 | Cu(OAc)₂ | 30 |
| 10 | CuSO₄ | 30 |

*determined by gas chromatography; m-phenoxytoluene (1.4 g) as internal standard 11. Example 2 was repeated, but 0.27 g (1.2 mmol) of Pd(OAc)₂ was employed instead of PdCl₂. 1.29 g (6.8 mmol) of butyl 3,3-dimethoxypropionate (57% of theory) were found by gas chromatography.

12. Example 2 was repeated, but 0.12 g (0.3 mmol) of PdCl₂(NCPh)₂ was employed instead of PdCl₂. 1.96 g (10.3 mmol) of butyl 3,3-dimethoxypropionate (86% of theory) were found by gas chromatography. After working up in accordance with Example 1, 2.0 g (10.5 mmol) of the product (88% of theory) were found by ¹H-NMRspectroscopy, in very good agreement with the gas chromatographic analysis.

13. Example 12 was repeated, but 5 g (109 mmol) of ethanol were employed instead of methanol. 2.25 g (9.8 mmol) of butyl 3,3-diethoxypropionate (82% of theory) are detected by gas chromatography.

14. Example 12 was repeated, but 10.2 g (108 mmol) of 3-chloropropanol were employed instead of methanol. 1.23 g (3.9 mmol) of butyl 3,3-di-(3'-chloropropoxy)propionate (33% of theory) are detected by gas chromatography.

15. Example 12 was repeated, but 1.03 g (12 mmol) of methyl acrylate were employed instead of butyl acrylate. 1.52 g (10.3 mmol) of methyl 3,3-dimethoxypropionate (85% of theory) were found by gas chromatography.

16. to 18. 0.07 g (0.4 mmol) of PdCl₂, 0.4 g (4 mmol) of CuCl, methanol in amounts corresponding to Table 3 and 0.51 g (4 mmol) of butyl acrylate were stirred for 20 hours at 50° C. under an O₂ atmosphere (O₂-filled air balloon) in a round-bottomed flask with a magnet core and reflux condenser. The yields of butyl 3,3-dimethoxypropionate as a function of the amount of methanol are collated in Table 3.

TABLE 3

| Ex. | Weight (CH₃OH) (g) | Yield (%*) |
| --- | --- | --- |
| 16 | 0.38 | 50 |
| 17 | 0.76 | 66 |
| 18 | 1.14 | 78 |

*determined by gas chromatography; m-phenoxytoluene (0.4 g) as internal standard 19. 0.12 g (0.3 mmol) of PdCl₂(NCPh)₂, 1.2 g (12 mmol) of CuCl, 10.26 g (321 mmol) of methanol and 3.06 g (24 mmol) of butyl acrylate in 21 g of dimethoxyethane were stirred for 20 hours at 50° C. under an O₂ atmosphere (O₂-filled air balloon) in a round-bottomed flask with a magnet core and reflux condenser. After addition of 2.4 g of m-phenoxytoluene, the mixture was worked up according to Example 1. 3.84 g (20.2 mmol) of butyl 3,3-dimethoxypropionate (84% of theory) are found by ¹H-NMR spectroscopy.

20. 0.12 g (0.3 mmol) of PdCl₂(NCPh)₂, 1.8 g (18 mmol) of CuCl, 4.6 g (36 mmol) of butyl acrylate and 15.4 g (481 mmol) of methanol were stirred for 20 hours at 50° C. under an O₂ atmosphere in 31.5 g of dimethoxyethane. After addition of 3.6 g of m-phenoxytoluene, the mixture was worked up as in Example 1. 5.74 g (30.2 mmol) of the product (84% of theory) are found in the residue by ¹H-NMR spectroscopy.

21. The procedure was initially as in Example 19. After 20 hours, a further 3.06 g (24 mmol) of butyl acrylate in 10.3 g (322 mmol) of methanol and 21 g of dimethoxyethane were added and the mixture was stirred for a further 20 hours at 50° C. under an O₂ atmosphere. After addition of 4.8 g of m-phenoxytoluene, the mixture was worked up as in Example 1. 7.56 g (39.7 mmol) of butyl 3,3-dimethoxypropionate (83% of theory) were found by ¹H-NMR spectroscopy.

22. Example 21 was repeated, but after a total of 40 hours a further 3.06 g (24 mmol) of butyl acrylate in 10.3 g of methanol and 21 g of dimethoxyethane were added. After a reaction time of 20 hours, 7.2 g of m-phenoxytoluene were added and the mixture was worked up according to Example 1. The yield of butyl 3,3-dimethoxypropionate is 11.4 g (59.9 mmol) (84% of theory).

23. Example 12 was repeated, but with acetonitrile as the solvent. After working up according to Example 1, 1.96 g (10.3 mmol) of butyl 3,3-dimethoxypropionate (86% of theory) were found by ¹H-NMR spectroscopy.

24. Example 1 was repeated, but 1.72 g (12 mmol) of CuBr were employed instead of CuCl. After working up according to Example 1, 1.64 g (8.6 mmol) of butyl 3,3-dimethoxypropionate (72% of theory) were found by 1H-NMR spectroscopy.

25. Example 1 was repeated, but 0.32 g (1.2 mmol) of PdBr₂ was employed instead of PdCl₂. After working up according to Example 1, 1.59 g (8.4 mmol) of butyl 3,3-dimethoxypropionate (70% of theory) were found by ¹H-NMR spectroscopy.

I claim:

1. A process for the preparation of 2-(dialkoxymethyl)carboxylic acid esters of the formula I

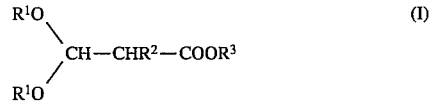

wherein

R¹ is a non-aromatic hydrocarbon radical or a heterocyclic non-aromatic radical, which apart from oxygen, nitrogen and/or sulfur atoms in the ring only contains carbon and hydrogen atoms, and each of which has 1 to 20 carbon atoms, it being possible for the radical R¹ to carry 1 to 5 substituents and the substituents being identical or different and being halogen, an aryl, carbalkoxy, dialkylamino, diarylamino or cyano group or an alkoxy groups, the alkyl being substituted or unsubstituted $C_1$- to $C_{12}$-alkyl, or is an aryloxy group, the aryl being substituted or unsubstituted $C_6$- to $C_{14}$-aryl, a substituted or unsubstituted benzyl or phenethyl radical or an R⁴O—(R⁵O)ₓ—R⁵ group, where R⁴ is substituted or unsubstituted $C_1$- to $C_{12}$-alkyl or $C_6$- to $C_{14}$-aryl, R⁵ is a branched or unbranched hydrocarbon radical having 1 to 4 carbon atoms or phenylene and x=1 to 6, R₂ is hydrogen or alkyl having 1 to 5 carbon atoms and R³ is unsubstituted or substituted $C_6$- to $C_{14}$-aryl or a radical mentioned under R¹, which comprises the step of:

conducting an oxidizing β-acetalization reaction of acrylic acid esters with alcohols R¹OH, wherein R¹ has the meaning mentioned, in the presence of:

an oxidant selected from the group consisting of pure oxygen or atmospheric oxygen a catalyst system containing one or more metals of the platinum group and/or compounds thereof and of a copper compound, said catalyst system containing 1 to 4 equivalents of anions, based on the sum of the metal atoms and the metal cations, of which at most 3 equivalents are halide ions, the halogen having a molecular weight of at least 35; at a temperature of up to 80° C.

2. The process as claimed in claim 1, wherein $R^2$ is hydrogen.

3. The process as claimed in claim 1, wherein the reaction is carried out in aliphatic or aromatic nitriles or diethers of glycols and other dihydric alcohols or of polymerization products of alcohols of this type as solvents.

4. The process as claimed in claim 3, wherein the solvent is dimethoxyethane, acetonitrile or benzonitrile.

5. The process as claimed in claim 1, wherein palladium and/or its compounds are employed as the metal of the platinum group and/or its compounds.

6. The process as claimed in claim 5, wherein a palladium halide $PdX_2$ or a palladium/nitrile complex $PdX_2(NCR)_2$ in which the halogen has a molecular weight of at least 35 and R is a hydrocarbon radical having 1 to 8 carbon atoms, is employed as the palladium compound.

7. The process as claimed in claim 1, wherein a copper(I) halide CuX, in which the halogen has a molecular weight of at least 35, is employed as the copper compound.

8. The process as claimed in claim 1, wherein the alcohol is employed in an at least two-fold molar amount relative to the acrylic acid ester.

9. The process as claimed in claim 1, wherein the metal of the platinum group and/or its compounds is employed in a molar ratio of $10^{-5}$ to 10 relative to the acrylic acid ester, the atomic ratio Cu to the metal of the platinum group preferably being at least 1:1.

10. The process as claimed in claim 1, wherein the copper(I) compound is employed in a molar ratio of $10^{-5}$ to 10 relative to the acrylic acid ester.

11. The process as claimed in claim 1, wherein the reaction is carried out at temperatures of above $-10°$ C.

12. The process as claimed in claim 1, wherein the alcohol is employed in an at least eight-fold molar amount relative to the acrylic acid ester.

13. The process as claimed in claim 1, wherein the metal of the platinum group and/or its compounds is employed in a molar ratio of $10^{-4}$ to 0.2, relative to the acrylic acid ester, the atomic ratio Cu to the metal of the platinum group being at least 1:1.

14. The process as claimed in claim 1, wherein the metal of the platinum group and/or its compounds is employed in a molar ratio of $10^{-3}$ to 0.1, relative to the acrylic acid ester, the atomic ratio Cu to the metal of the platinum group being at least 1:1.

15. The process as claimed in claim 1, wherein the copper(I) compound is employed in a molar ratio of $10^{-3}$ to 5, relative to the acrylic acid ester.

16. The process as claimed in claim 1, wherein the copper(I) compound is employed in a molar ratio of 0.01 to 1, relative to the acrylic acid ester.

17. The process as claimed in claim 1, wherein the reaction is carried out at temperatures of between $+10°$ to $70°$ C.

18. The process as claimed in claim 1, wherein the reaction is carried out at temperatures of between $+20°$ to $55°$ C.

19. A process for the preparation of 2-(dialkoxymethyl)carboxylic acid esters of the formula I

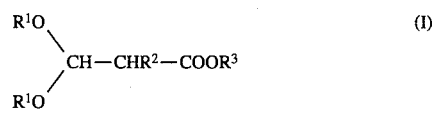

wherein $R^1$ is a non-aromatic hydrocarbon radical or a heterocyclic non-aromatic radical, which apart from oxygen, nitrogen and/or sulfur atoms in the ring only contains carbon and hydrogen atoms, and each of which has 1 to 20 carbon atoms, it being possible for the radical $R^1$ to carry 1 to 5 substituents and the substituents being identical or different and being halogen, an aryl, carbalkoxy, dialkylamino, diarylamino or cyano group or an alkoxy group, the alkyl being substituted or unsubstituted $C_1$- to $C_{12}$ alkyl, or is an aryloxy group, the aryl being substituted or unsubstituted $C_6$- to $C_{14}$-aryl, a substituted or unsubstituted benzyl or phenethyl radical or an $R^4O$—$(R^5O)_x$—$R^5$ group, where $R^4$ is substituted or unsubstituted $C_1$- to $C_{12}$-alkyl or $C_6$- to $C_{14}$-aryl, $R^5$ is a branched or unbranched hydrocarbon radical having 1 to 4 carbon atoms or phenylene and x=1 to 6, $R^2$ is hydrogen or alkyl having 1 to 5 carbon atoms and $R^3$ is unsubstituted or substituted $C_6$- to $C_{14}$-aryl or a radical mentioned under $R^1$, by oxidizing β-acetalization of acrylic acid esters with alcohols $R^1OH$, wherein $R^1$ has the meaning mentioned, in the presence of an oxidant consisting of oxygen and of a catalyst system containing one or more metals of the platinum group and/or compounds thereof and of a copper compound, comprises carrying out the reaction at a temperature of up to 70° C. and in which the catalyst system contains 1 to 4 equivalents of anions, based on the sum of the metal atoms and metal cations, of which at most 3 equivalents are halide ions, the halogen having molecular weight of at least 35.

* * * * *